(12) United States Patent
Nozato

(10) Patent No.: US 8,273,529 B2
(45) Date of Patent: Sep. 25, 2012

(54) METHOD FOR HYBRIDIZING NUCLEIC ACIDS AND HYBRIDIZATION APPARATUS

(75) Inventor: Koji Nozato, Yokohama (JP)

(73) Assignee: Canon Kabushiki Kaisha, Tokyo (JP)

( * ) Notice: Subject to any disclaimer, the term of this patent is extended or adjusted under 35 U.S.C. 154(b) by 462 days.

(21) Appl. No.: 11/702,594

(22) Filed: Feb. 6, 2007

(65) Prior Publication Data

US 2007/0184479 A1 Aug. 9, 2007

(30) Foreign Application Priority Data

Feb. 8, 2006 (JP) ................................. 2006-031046

(51) Int. Cl.
*C12Q 1/68* (2006.01)
(52) U.S. Cl. ....................................................... 435/6.1
(58) Field of Classification Search ........................ None
See application file for complete search history.

(56) References Cited

U.S. PATENT DOCUMENTS

| | | | |
|---|---|---|---|
| 5,474,796 A | * 12/1995 | Brennan | 427/2.13 |
| 6,238,910 B1 | 5/2001 | Custance et al. | 435/287.2 |
| 6,410,235 B1 | * 6/2002 | Weindel et al. | 435/6 |
| 6,476,215 B1 | 11/2002 | Okamoto et al. | 536/25.3 |
| 2003/0162283 A1 | 8/2003 | Kuno et al. | 435/287.2 |
| 2005/0130185 A1 | * 6/2005 | Lu et al. | 435/6 |

FOREIGN PATENT DOCUMENTS

| | | | |
|---|---|---|---|
| CN | 1248702 A | * | 3/2000 |
| JP | 11-187900 | | 7/1999 |
| JP | 2003-315337 | | 11/2003 |

OTHER PUBLICATIONS

Schena et al. (Science. Oct. 20, 1995;270(5235):467-70).*

* cited by examiner

*Primary Examiner* — Christopher M. Babic
(74) *Attorney, Agent, or Firm* — Fitzpatrick, Cella, Harper & Scinto

(57) ABSTRACT

A method for hybridizing a target nucleic acid and a probe nucleic acid that can specifically bind to the target nucleic acid and that is immobilized on a substrate includes a first reaction step of allowing the target nucleic acid contained in a sample solution to react with the probe nucleic acid, a recovery step of recovering the sample solution after the first reaction step, a heating step of heating the recovered sample solution to the denaturation temperature of the target nucleic acid or a higher temperature, and a second reaction step of allowing the target nucleic acid contained in the sample solution after the heating step to react with the probe nucleic acid.

5 Claims, 8 Drawing Sheets

METHOD FOR HYBRIDIZING NUCLEIC ACIDS AND HYBRIDIZATION APPARATUS

BACKGROUND OF THE INVENTION

1. Field of the Invention

The present invention relates to a method of detecting the quantity or the presence or absence of a target nucleic acid using a hybridization reaction of a probe nucleic acid immobilized on a substrate and a nucleic acid contained in a sample.

2. Description of the Related Art

As genome sequencing projects advance, for example, detection of specific genes in genome sequences, analysis of single nucleotide polymorphisms (SNPs), and expression analysis of genes have attracted attention as post-genome challenges. Accordingly, in the fields of recent medicine and molecular biology, the importance of analysis methods such as a microarray hybridization method and an in situ hybridization method has been increasing as methods of detecting a target sequence. In the microarray hybridization method and the in situ hybridization method, a nucleic acid probe that specifically binds to a target substance is immobilized on a substrate, and the nucleic acid probe and a sample are hybridized, thus determining the presence of the target substance in the sample.

In general, these hybridization reactions are conducted by dripping a hybridization solution containing a sample on a substrate on which a nucleic acid probe is immobilized. In this process, the substrate is covered with a cover glass so that the hybridization solution does not evaporate. The substrate is then placed in a wet box or a sealed cassette and incubated at a constant temperature for a long time (4 to 50 hours).

However, in the above method of covering with a cover glass, since the hybridization solution on the substrate negligibly moves, the collision frequency between the probe immobilized on the substrate and the sample in the solution is low, resulting in a significantly low hybridization efficiency. Accordingly, it takes a long time to conduct the hybridization reaction, and the method causes a problem in the reliability of data due to uneven hybridization.

In order to increase the hybridization efficiency and to improve the uniformity of hybridization, hybridization ovens having a seesaw-type or roller bottle-type solution-shaking function have been used. However, these hybridization ovens cannot provide a satisfactory effect.

Consequently, hybridization apparatuses aiming at a reduction in the reaction time and an improvement in the uniformity have been recently developed.

An example of such an apparatus is disclosed in U.S. Pat. No. 6,238,910. In this apparatus, a hybridization solution held as a reaction layer is agitated with air (the solution is subjected to a reciprocating shaking), thereby increasing the hybridization efficiency. However, in the mixing by agitation as in this apparatus, it is difficult to maintain the uniformity of the substrate over the entire surface. In addition, once air bubbles are mixed in the apparatus, the air bubbles cannot be eliminated, resulting in an unevenness of hybridization.

Consequently, as disclosed in Japanese Patent Laid-Open No. 2003-315337, a hybridization apparatus in which a reaction solution is circulated in a passage including a substrate has been developed. According to the description of this patent document, the circulation increases the collision frequency between a probe and a sample, and advantages of an increase in the hybridization efficiency and an improvement in the uniformity of hybridization can be achieved.

However, any of these methods is unsatisfactory from the standpoint that the efficiency of the reaction treatment is increased. This is because all the above-described methods are performed on the premise that a complementary strand in the sample solution does not affect the hybridization reaction. That is, these methods require a step of relatively decreasing the complementary strand nucleic acid of the target nucleic acid. Examples of this treatment include an asymmetric polymerase chain reaction (PCR) method using a single-stranded primer and other methods, but these treatments are time-consuming and complex.

SUMMARY OF THE INVENTION

The present invention provides a novel method for hybridizing nucleic acids in which a conventional step of removing a complementary strand before the hybridization reaction is not required and a target nucleic acid can be efficiently trapped with a probe nucleic acid, and a hybridization apparatus therefor.

Namely, according to a method of the present invention, a method for hybridizing a target nucleic acid and a probe nucleic acid that can specifically bind to the target nucleic acid and that is immobilized on a substrate includes a first reaction step of allowing the target nucleic acid contained in a sample solution to react with the probe nucleic acid, a recovery step of recovering the sample solution after the first reaction step, a heating step of heating the recovered sample solution to the denaturation temperature of the target nucleic acid or a higher temperature, and a second reaction step of allowing the target nucleic acid contained in the sample solution after the heating step to react with the probe nucleic acid.

According to an apparatus of the present invention, a hybridization apparatus for hybridizing a target nucleic acid and a probe nucleic acid that can specifically bind to the target nucleic acid and that is immobilized on a substrate includes a setting section for setting the substrate, a supply path for supplying the substrate with a sample solution containing the target nucleic acid, a recovery mechanism for recovering the supplied sample solution, and a heater for heating the sample solution recovered by the recovery mechanism to the denaturation temperature or higher, wherein the recovery mechanism is configured so as to again supply the heated sample solution to the substrate.

According to a cartridge of the present invention, a cartridge in which a probe nucleic acid that can specifically bind to a target nucleic acid is immobilized includes a reaction chamber for accommodating the probe nucleic acid, a supply port for supplying the reaction chamber with a sample solution containing the target nucleic acid, and a recovery section for recovering the sample solution supplied to the reaction chamber.

According to an analysis apparatus of the present invention, an analysis apparatus for hybridizing a labeled target nucleic acid and a probe nucleic acid that can specifically bind to the target nucleic acid and that is immobilized on a substrate and for detecting a label present on the substrate includes a setting section for setting the substrate, a supply path for supplying the substrate with a sample solution containing the target nucleic acid, a recovery mechanism for recovering the sample solution, a heater for heating the sample solution recovered by the recovery mechanism to the denaturation temperature or higher, and a detector for detecting the label, wherein the recovery mechanism is configured so as to again supply the heated sample solution to the substrate.

According to the method for hybridizing nucleic acids and the hybridization apparatus of the present invention, a sample containing a double-stranded nucleic acid amplified by a PCR amplification process or the like can be provided to a hybridization reaction without removing the complementary strand. Accordingly, a target nucleic acid can be detected more efficiently compared with known techniques.

Further features of the present invention will become apparent from the following description of exemplary embodiments with reference to the attached drawings.

DESCRIPTION OF THE EMBODIMENTS

Before the present invention is described in detail, terms relating to the present invention are defined as follows.

The term "denaturation temperature" is defined as a temperature at which the double helix structure of a double-stranded nucleic acid is denatured and separated into single strands. When a double-stranded DNA is heated to 90° C. or higher, a change in a physical property due to the structural change is observed. The midpoint of the change in the physical property may be simplistically defined as the denaturation temperature, but the change in the physical property occurs in a considerably narrow temperature range. Therefore, in the present invention, the denaturation temperature may also include a temperature at which the change in the physical property is started.

The term "hybridization temperature" means a temperature at which a hybridization reaction is conducted. A suitable temperature condition is appropriately set on the basis of conditions such as the base length of a target nucleic acid and the type of reagent used.

Specific embodiments of a method for hybridizing nucleic acids and a hybridization apparatus according to the present invention will now be described, but the present invention is not limited to these embodiments.

First Embodiment

Figure 1:
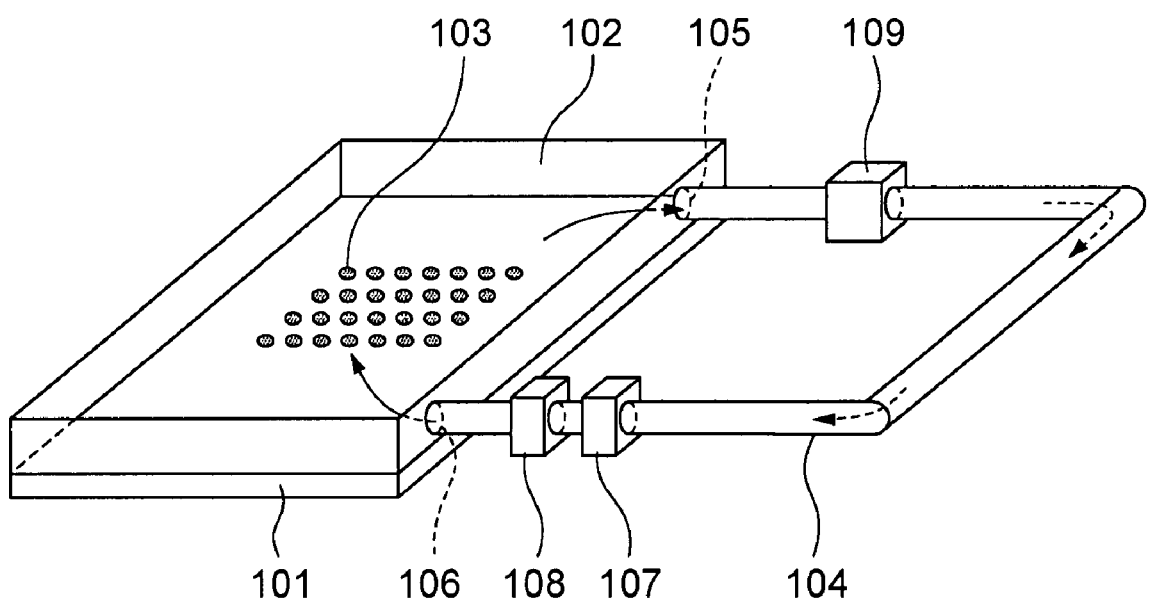
FIG. 1 is a schematic view showing an apparatus suitably used for performing a method of the present invention.

FIG. 1 is a schematic view showing an example of a hybridization apparatus of the present invention. The hybridization apparatus shown in FIG. 1 includes a substrate 101 for immobilizing a probe nucleic acid and a chamber (reaction chamber) 102 including microspaces for holding a reaction solution containing a target nucleic acid. A probe nucleic acid 103 that specifically binds to the target nucleic acid is disposed on the substrate 101. The chamber 102 includes an outlet 105 and an inlet 106 of the reaction solution, and the outlet 105 and the inlet 106 are connected by a passage 104 serving as a circulation unit. A pump 109 serving as a supply unit and a recovery unit is provided in the passage 104 and circulates the reaction solution (not shown). A first temperature control unit 107 and a second temperature control unit 108 are also provided in the passage 104 and control the temperature of the circulating reaction solution. Furthermore, the temperature of the substrate 101 can also be controlled with a heater or the like (not shown).

Figure 2A:
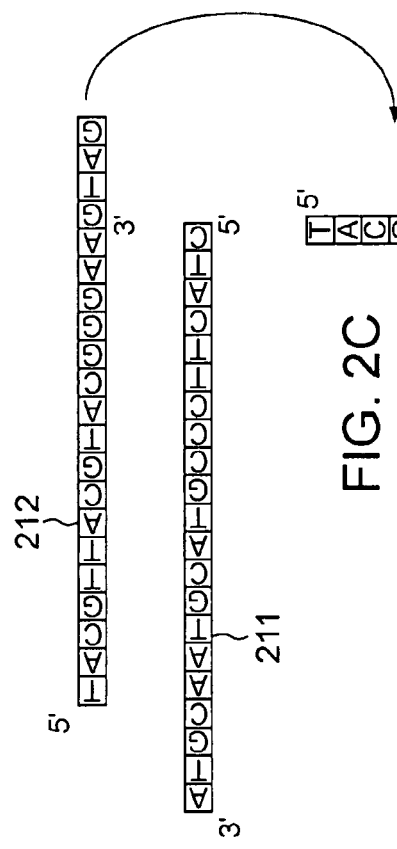
FIGS. 2A to 2C are schematic views showing the outline of a hybridization reaction.
Figure 2B:
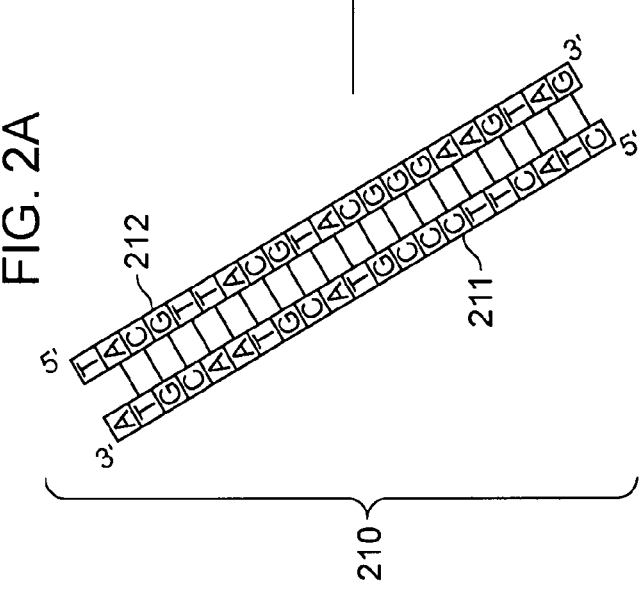
Figure 2C:
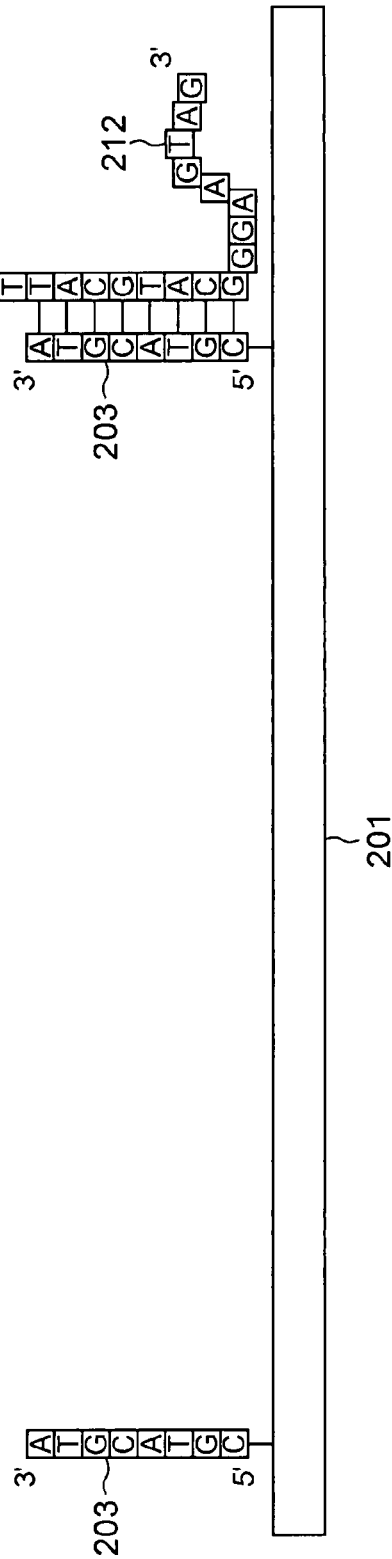

The outline of a hybridization method will now be described with reference to FIGS. 2A to 2C. FIGS. 2A to 2C show an example in which a target nucleic acid is a double-stranded DNA. Alternatively, the target nucleic acid may be, for example, an RNA or a single-stranded DNA such as a complementary DNA (cDNA). FIG. 2A shows a double-stranded target nucleic acid 210. The target nucleic acid 210 is constituted by combining a sense strand 211 and an antisense strand 212 that have base sequences complementary to each other. For example, a probe nucleic acid 203 having a base sequence complementary to the base sequence of the antisense strand 212, which is one strand of the target nucleic acid 210, is immobilized on a substrate 201. A hybridization solution containing the target nucleic acid 210 is brought into contact with the substrate 201 on which the probe nucleic acid 203 is immobilized. The reaction solution is then heated to about 95° C., thereby separating the double-stranded nucleic acid into the sense strand 211 and the antisense strand 212, as shown in FIG. 2B. The temperature of the reaction solution is then controlled to an optimum temperature for hybridization. Consequently, as shown in FIG. 2C, the antisense strand 212 of the target nucleic acid is bound to the probe nucleic acid 203. Although the optimum temperature is different depending on the type of probe nucleic acid 203 used, the optimum temperature is in the range of about 30° C. to 60° C. After the reaction is conducted at the optimum temperature for several hours, the substrate is washed with an appropriate cleaning solution to remove the target nucleic acid 210 that does not bind to the probe nucleic acid 203, etc. Subsequently, the presence or absence of a target sequence is determined by detecting the antisense strand 212 of the target nucleic acid remaining on the substrate. Examples of the detection method include a method in which the target nucleic acid 210 is labeled with a fluorescent dye or a radioactive substance in advance and the fluorescent dye or the radioactive substance is observed after hybridization, and a method of observing the hybridization binding with the probe nucleic acid 203 using an intercalator dye such as Cyber-Green. Furthermore, even when a labeled substance is suspended in the chamber, the substance can be detected in a liquid layer with a confocal microscope.

A probe nucleic acid is specifically recognized by a specific target and often referred to as a ligand. Furthermore, this probe includes oligonucleotides, polynucleotides, and other polymers that can be recognized by a specific target. In some cases, the term "probe" means a probe molecule itself having a probe function, e.g., individual polynucleotide molecules. In some cases, the term "probe" means a group of probe molecules having the same probe function, e.g., polynucleotides that have the same sequence and that are immobilized on a surface of a carrier in a dispersed state or the like. The probe is a substance that can be bound with or can become to bind with a target as a part of a ligand/anti-ligand pair. The probe and the target in the present invention can include bases that can be found in nature and analogues thereof.

The probe used in the method of the present invention is appropriately selected in accordance with the intended use. In order to suitably perform the method of the present invention, the probe can be a DNA, an RNA, a cDNA, a PNA, an oligonucleotide, a polynucleotide, or other nucleic acid. These may be used in combinations of two or more substances according to need.

As a probe nucleic acid in the hybridization method, an artificially-synthesized oligo DNA, BAC DNA synthesized by a vector such as bacteria, cDNA, or the like is used. Regarding the base length of the probe nucleic acid, the base length of a short-chain oligo DNA can be in the range of about 20 to 60 mer, and the base length of a long-chain BAC DNA can be about several kmer.

The probe 203 is often immobilized on the substrate 201 with a linker (not shown) therebetween. In an amino-modified oligonucleotide, poly-L-lysine is often used as the linker. In an SH group-modified oligonucleotide, for example, a surface of a slide glass is treated with an aminosilane coupling agent, and the oligonucleotide can then be immobilized in a solid phase with a bifunctional reagent such as N-(6-maleimidocaproyloxy)succinimide (EMCS). In addition to the methods of binding a prepared probe nucleic acid on a substrate, a method of synthesizing a nucleic acid on a substrate by photolithography may also be employed.

The substrate 201 is generally made of glass such as quartz or borosilicate glass or a resin, or may be made of a non-woven fabric or the like. A plate-shaped substrate is used in FIG. 1, but the shape of the substrate is not limited thereto. The substrate may form a cylindrical passage or may be a filter that transmits the reaction solution. Alternatively, a plurality of particulate substrates immobilizing the probe nucleic acid 103 may be included in the chamber 102.

The shape and the material of the chamber 102 are not particularly limited as long as the reaction solution can be held on the substrate 101. When the hybridization apparatus is configured so that the state of the substrate 101 is observed through the chamber 102, a material suitable for the observation unit is used as the chamber 102. The substrate 101 may have a shape so as to also function as a chamber. The passage 104 is connected to the chamber 102 through the outlet 105 and the inlet 106. The shapes of the outlet 105 and the inlet 106 are not particularly limited as long as the reaction solution flows at a desired flow rate. Furthermore, the chamber 102 can have an injection port for injecting a reaction solution from the outside and a temperature control function for controlling the temperature of the substrate 101.

The shape and the material of the passage 104 are not particularly limited as long as the outlet 105 and the inlet 106 of the chamber 102 can be connected with each other. The reaction solution is circulated in the passage 104 by the pump 109. A part of the passage 104 may have an irregular-shaped cross section. In such a case, the flow rate of the reaction solution can be adjusted. Furthermore, a buffer area may be provided in the passage so that the reaction solution is temporarily retained.

A feature of this embodiment lies in the first temperature control unit 107 and the second temperature control unit 108 provided in appropriate positions in the passage 104. The mechanism and the shape of these temperature control units are not particularly limited as long as the temperature of the reaction solution in the passage can be increased or decreased. For example, Peltier elements may be disposed at the outer periphery of the passage. The first temperature control unit 107 must have an appropriate shape so that the temperature of the reaction solution is controlled to a temperature (denaturation temperature) required for separating the double strand of the target nucleic acid for a predetermined time. The second temperature control unit 108 must have an appropriate shape so that the temperature of the reaction solution is controlled to an optimum temperature for the hybridization of the probe nucleic acid and the target nucleic acid. Furthermore, the time required for the reaction solution, which was passed through the second temperature control unit 108, to reach the substrate 101 must be shorter than the time required for the reaction for forming a double strand of the target nucleic acid to reach the equilibrium state. For example, when double-stranded DNA molecules are incubated at the melting temperature tm, half of the DNA molecules are separated into single-stranded DNA molecules. The period required for half of the single-stranded DNA molecules to form the double-stranded DNA molecules is represented by the following equation.

Half-life of single strand=LN2/(binding rate constant× initial concentration of target nucleic acid+dissociation rate constant) (Equation 1)

Although the binding rate constant is different depending on the structure of DNA, the binding rate constant at a temperature lower than the melting temperature tm is generally about $10^4$ to $10^7$ $M^{-1}s^{-1}$. When the initial concentration is 10 nM and the dissociation is ignored (dissociation rate=0), the half-life is 7 seconds. Actually, since diffusion affects the reaction (diffusion constant: about $10^{-11}$ $m^2/s$) and a dissociation reaction, which is the reverse reaction, also proceeds, the half-life is increased by several orders of magnitude. Accordingly, for example, the shape and the flow rate of the passage are set so that the reaction solution is supplied from the second temperature control unit 108 to the substrate 101 within 7 seconds.

Figure 3:
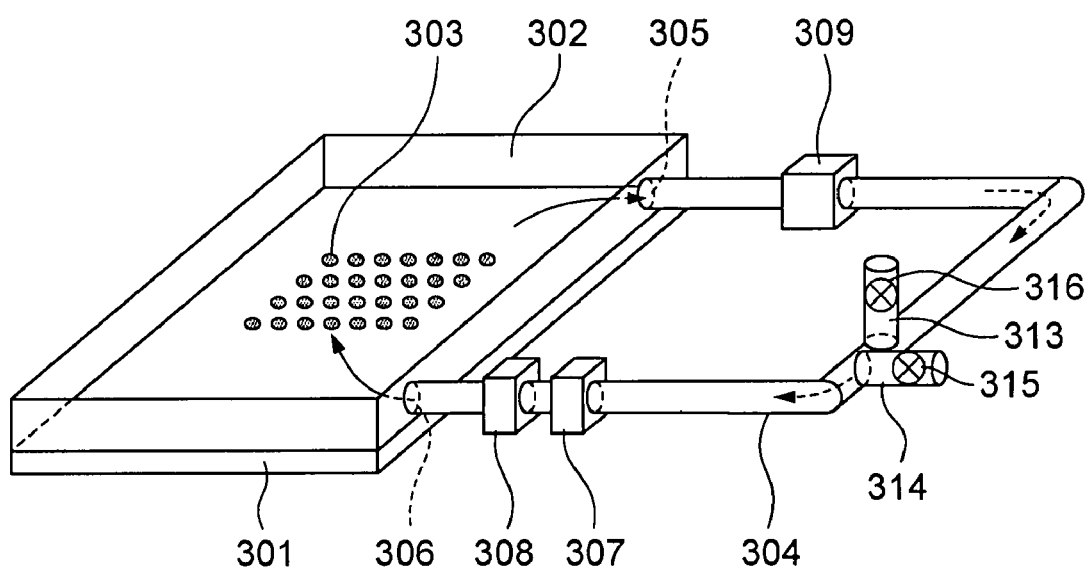
FIG. 3 is a schematic view showing an apparatus suitably used for performing the method of the present invention.

The flow of the hybridization method of this embodiment will now be described with reference to FIG. 3. FIG. 3 shows an example of a hybridization apparatus of this embodiment, and the structure of this apparatus is similar to that of the apparatus shown in FIG. 1. First, a target nucleic acid is labeled with a fluorescent dye. The labeled target nucleic acid is used for preparing a hybridization solution having an appropriate composition. For example, the composition of the hybridization solution includes a buffer solution such as SSPE, a denaturing agent such as formamide, and an antifoaming agent. An oligo DNA having a sequence complementary to that of the target nucleic acid is immobilized as a probe nucleic acid 303 on a substrate 301. The substrate 301 is joined to a chamber 302, which includes an inlet 306 and an outlet 305. A valve 315 of an injection port 314 on a passage 304 and a valve 316 of an air vent 313 are opened. The hybridization solution is injected into the passage 304 through the injection port 314. In the injection process, the passage 304 and the chamber 302 are filled with the hybridization solution, and the hybridization solution is discharged from the air vent 313. The valves 315 and 316 are closed at the time when the chamber 302 and the passage 304 are filled with the hybridization solution. The temperature of the substrate 301 is controlled to a temperature t1 that is the optimum temperature for hybridization. Although the temperature t1, which is the optimum temperature for hybridization, is different depending on the types of probe nucleic acid 303 and target nucleic acid used, the temperature t1 is about 50° C. A first temperature control unit 307 controls the temperature of the hybridization solution to the denaturation temperature t2 of the target nucleic acid. Although the denaturation temperature t2 is different depending on the type of target nucleic acid used, the denaturation temperature t2 is about 95° C. A second temperature control unit 308 controls the temperature of the hybridization solution to the temperature t1, which is the optimum temperature for hybridization. A pump 309 is operated, and the hybridization solution is circulated in the passage 304 in the clockwise direction on the figure. The black arrows in the figure indicate the circulation direction of the hybridization solution. The target nucleic acid is separated into single strands by the first temperature control unit 307, and the temperature of the single-stranded target nucleic acid is immediately controlled to the temperature t1 by the second temperature control unit 308. The single-stranded target nucleic acid reaches the chamber 302 before the double strand of the target nucleic acid itself is produced. The single-stranded target nucleic acid is then brought into contact with the probe nucleic acid 303 to perform a hybridization reaction. Even when the single-stranded target nucleic acids form a double strand during the hybridization reaction, the double strand is again separated into single strands by the first temperature control unit 307 during the circulation in the passage. The resulting single strands are again brought into contact with the probe nucleic acid 303, and the hybridization reaction proceeds. As described above, according to the present invention, a double-stranded target nucleic acid, which does not contribute to the hybridization reaction by known techniques, can be brought into contact with the probe nucleic acid 303 again while being in a state in which the target nucleic acid can be hybridized. Accordingly, the efficiency and the sensitivity of hybridization can be improved. About 1 to 50 hours later, the pump 309 is stopped and the substrate 301 is removed. The fluorescent dye in the target nucleic acid bound to the probe nucleic acid 303 on the substrate 301 is observed with an appropriate microscope.

Figure 7:
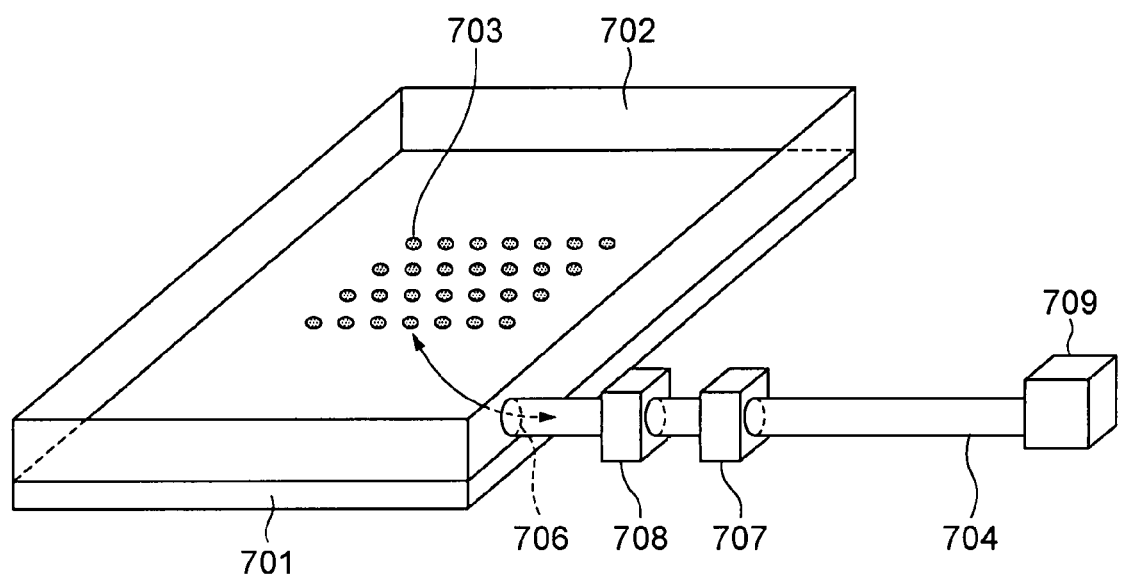
FIG. 7 is a schematic view showing an apparatus suitably used for performing a method of the present invention.

In addition to the circulation system of a sample solution using the passage 104 or 304, other structures may be used. For example, as shown in FIG. 7, a temperature control mechanism may be provided in a passage connecting a reaction chamber to a pump. The hybridization apparatus shown in FIG. 7 includes: a substrate 701 having a probe nucleic acid 703 disposed thereon; a chamber 702 having an inlet/outlet 706; a first temperature control unit 707; a second temperature control unit 708; a passage 704; and a pump 709. Accordingly, recovery and supply can be repeatedly performed. In this case, a syringe pump can be used as the pump.

In general, when a target nucleic acid and its complementary strand are present, the target nucleic acid forms a double strand with the complementary strand, and the ratio of a single-stranded nucleic acid that can be bound to a probe nucleic acid to the total nucleic acid is significantly low. Therefore, a hybridization reaction with the probe does not easily occur. Since the chain of the target nucleic acid is longer than that of the probe nucleic acid, the probability (amount) of the occurrence of the hybridization reaction with the probe nucleic acid is further decreased in the equilibrium state. Even if the reaction solution is heated to a temperature at which the double strand is separated prior to the hybridization, a double strand is again formed when the temperature of the reaction solution is decreased to the optimum temperature of the hybridization. Consequently, the number of single strands that contributes to the hybridization reaction with the probe is small, resulting in a significantly low reaction rate. Since this problem can be solved in this embodiment, the efficiency and the sensitivity of hybridization can be realized.

Second Embodiment

Figure 4:
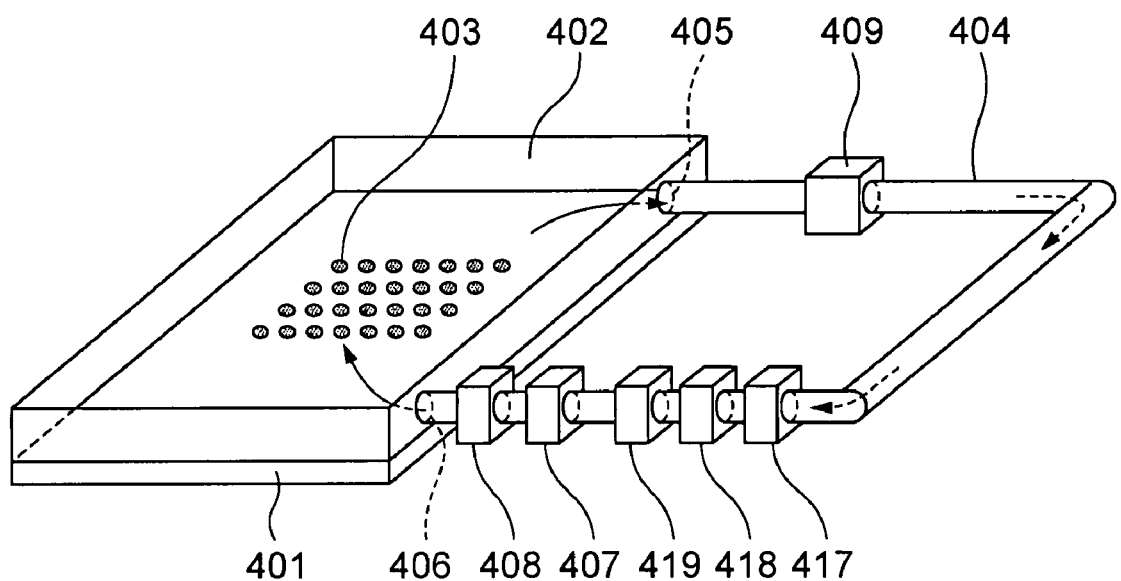
FIG. 4 is a schematic view showing an apparatus suitably used for performing a method of the present invention.

Another embodiment of the present invention will now be described with reference to FIG. 4. FIG. 4 shows an example of an apparatus in which a hybridization reaction is conducted while a target nucleic acid is simultaneously amplified. The apparatus shown in FIG. 4 includes a substrate 401 for immobilizing a probe nucleic acid and a chamber 402 including microspaces for holding a reaction solution containing a target nucleic acid and a PCR reagent. A probe nucleic acid 403 that specifically binds to the target nucleic acid is disposed on the substrate 401. The chamber 402 includes an outlet 405 and an inlet 406 of the reaction solution, and the outlet 405 and the inlet 406 are connected by a passage 404. A pump 409 is provided in the passage 404 and circulates the reaction solution (not shown). A first temperature control unit 407 and a second temperature control unit 408 are also provided in the passage 404 and control the temperature of the circulating reaction solution. A feature of this apparatus lies in a third temperature control unit 417, a fourth temperature control unit 418, and a fifth temperature control unit 419 for controlling the temperature of the circulating reaction solution to temperatures optimum for each step of PCR.

The flow of a hybridization method in the case where the apparatus shown in FIG. 4 is used will now be described. A target nucleic acid is used for preparing a hybridization solution having an appropriate composition containing a reagent required for PCR. The PCR reagent is a reagent used in a PCR reaction and includes, for example, the following.

1. A primer DNA that specifically binds to either end of the amplification site of a target sequence.
2. A DNA polymerase that synthesizes a DNA complementary to the target sequence from the primer bound to a target nucleic acid.
3. Various nucleotides required for DNA synthesis.
4. Salts such as magnesium chloride and potassium chloride.
5. A buffer solution such as a Tris buffer.

For example, the composition of a hybridization solution includes a buffer solution, a denaturing agent such as formamide, and an antifoaming agent. Components that do not inhibit the function of the above PCR reagent can be used as these components. The hybridization solution may contain a labeled primer, an intercalator such as Cyber-Green, and a labeled nucleotide in order to detect hybridization. The substrate 401 on which the probe nucleic acid 403 is immobilized is joined to the chamber 402. The hybridization solution is injected into in the passage 404 as in the above embodiment. The temperature of the substrate 401 is controlled to a temperature t1 that is the optimum temperature for hybridization. Although the temperature t1, which is the optimum temperature for hybridization, is different depending on the types of probe nucleic acid 403 and target nucleic acid used, the temperature t1 is about 50° C. The first temperature control unit 407 controls the temperature of the hybridization solution to the denaturation temperature t2 of the target nucleic acid. Although the denaturation temperature t2 is different depending on the type of target nucleic acid used, the denaturation temperature t2 is about 95° C. The second temperature control unit 408 controls the temperature of the hybridization solution to the temperature t1, which is the optimum temperature for hybridization. The third, fourth, and fifth temperature control units control the temperature of the hybridization solution to optimum temperatures for each step of PCR. Regarding the optimum temperatures for each step of PCR, the denaturation temperature of the target double strand is about 95° C., the annealing temperature of the single-stranded target nucleic acid and the primer is about 60° C., and the temperature during the extension reaction is about 72° C. The third, fourth, and fifth temperature control units are set so that the temperatures are controlled to about 95° C., 60° C., and 72° C., respectively. The pump 409 is operated, and the hybridization solution is circulated in the passage 404 in the clockwise direction on the figure. The black arrows in the figure indicate the circulation direction of the hybridization solution. The target nucleic acid is separated into single strands by the third temperature control unit 417. The temperature of the single-stranded target nucleic acid is then controlled to the annealing temperature by the fourth temperature control unit 418, and the single-stranded target nucleic acid is annealed with the primer nucleic acid in the reaction solution. Subsequently, the extension reaction proceeds from the primer in the fifth temperature control unit 419 to amplify the target nucleic acid. The double-stranded target nucleic acid produced by the amplification is again separated into single strands by the first temperature control unit 407, and the temperature of the single-stranded target nucleic acid is immediately controlled to the temperature t1 by the second temperature control unit 408. The single-stranded target nucleic acid reaches the chamber 402 before the double strand of the target nucleic acid itself is produced. The single-stranded target nucleic acid is then brought into contact with the probe nucleic acid 403 to perform a hybridization reaction. The target nucleic acid in the reaction solution passed through the chamber 402 is again amplified by the third, fourth, and fifth temperature control units and is then circulated in the chamber 402. About 1 to 50 hours later, the pump 409 is stopped and the substrate 401 is removed. For example, the fluorescent dye in the target nucleic acid bound to the probe nucleic acid 403 on the substrate 401 is observed with an appropriate microscope. As described above, since the hybridization reaction and the PCR reaction proceed at the same time, the presence or absence of the target nucleic acid can be detected with high sensitivity even in a very small amount of sample. Furthermore, the apparatus may have a structure in which the state during the PCR reaction and the hybridization reaction can be observed.

Figure 5:
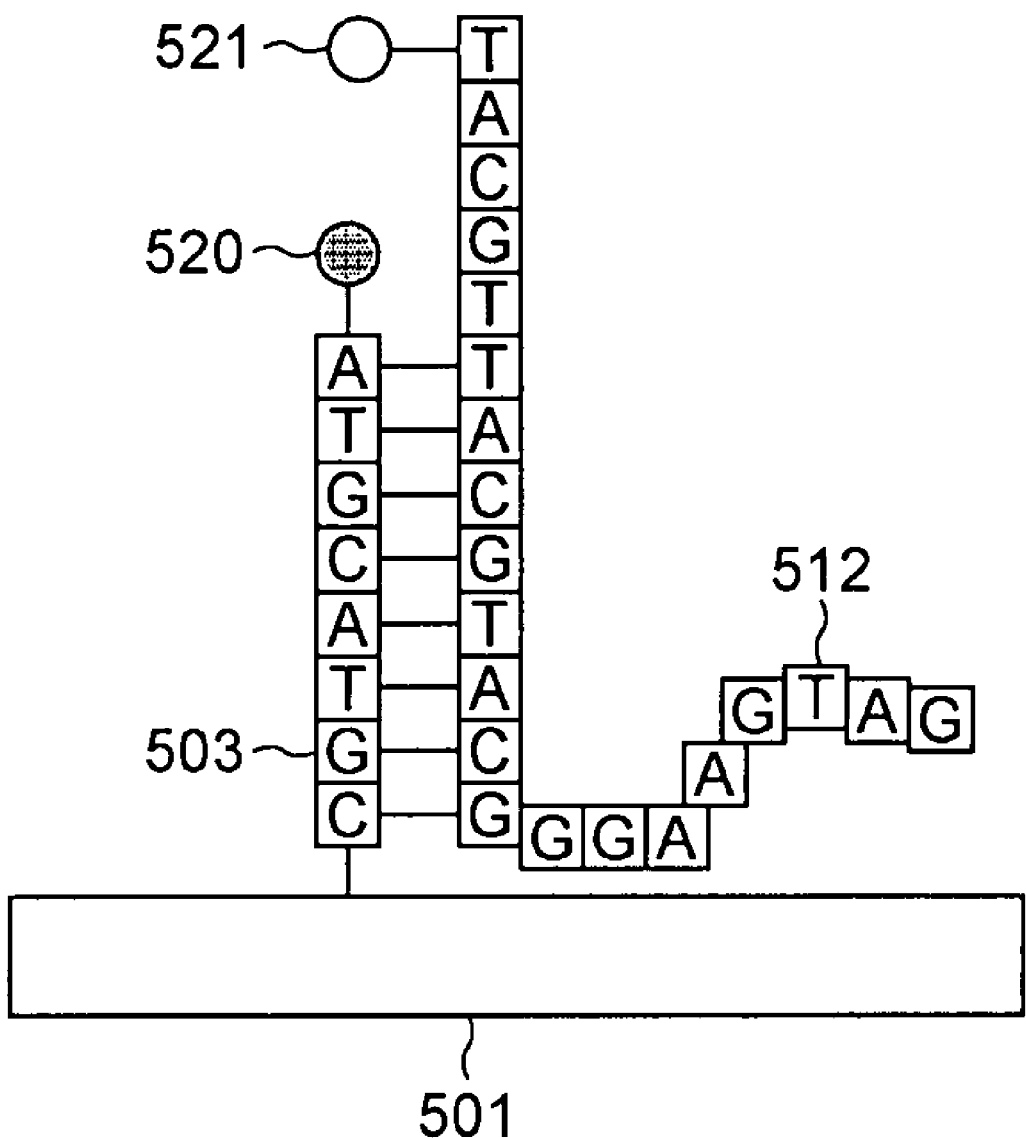
FIG. 5 is a schematic view showing the outline of a detection method of the present invention.

Next, a method of detecting hybridization according to this embodiment will now be described with reference to FIG. 5. A probe nucleic acid 503 is immobilized on a substrate 501. The probe nucleic acid 503 has a nucleic acid sequence that specifically binds to a target nucleic acid 512. A feature of this embodiment lies in a first dye 520 labeled on the probe nucleic acid 503 and a second dye 521 labeled on the target nucleic acid 512. The first dye 520 and the second dye 521 are a pair of fluorescent dyes that can cause a fluorescence resonance energy transfer (FRET). The first dye 520 and the second dye 521 may be bound to any position of the probe nucleic acid 503 or the target nucleic acid 512, but the first dye 520 and the second dye 521 must be disposed within a certain distance so that the dyes can induce the FRET phenomenon when being bound to each other. The FRET is a phenomenon in which excitation energy is transferred from a fluorescent molecule (donor molecule) to another molecule (acceptor molecule). Since the FRET phenomenon occurs only when the donor molecule and the acceptor molecule are close to each other (generally within 50 to 100 Å), the fluorescence intensity observed from the outside is varied in accordance with the distance between the compounds. As shown in FIG. 5, when the probe nucleic acid 503 is labeled with the first dye 520 serving as a donor dye and the target nucleic acid 512 is labeled with the second dye 521 serving as an acceptor dye, the FRET phenomenon occurs and fluorescence is emitted only in the case where the probe nucleic acid 503 is bound to the target nucleic acid 512. In the target nucleic acid 512 that is not bound to the probe nucleic acid 503, fluorescence is not emitted because the FRET phenomenon does not occur. Accordingly, the effect of the target nucleic acid that is not bound to the probe nucleic acid can be eliminated even in a reaction solution containing the labeled target nucleic acid, and thus the binding between the probe nucleic acid and the target nucleic acid can be accurately detected.

A feature of this embodiment lies in that the PCR amplification step and the hybridization step, which are performed in separated structures using known apparatuses, are performed in a single structure. This is advantageous in that, for example, the effect of a solution mixing (contamination) due to the transfer of liquids during the steps can be decreased.

Accordingly, a preliminary treatment for amplifying the nucleic acid is not required even in a very small amount of sample. Thus, the operation can be simplified, the risk of contamination can be eliminated, and the process time can be reduced.

Figure 6:
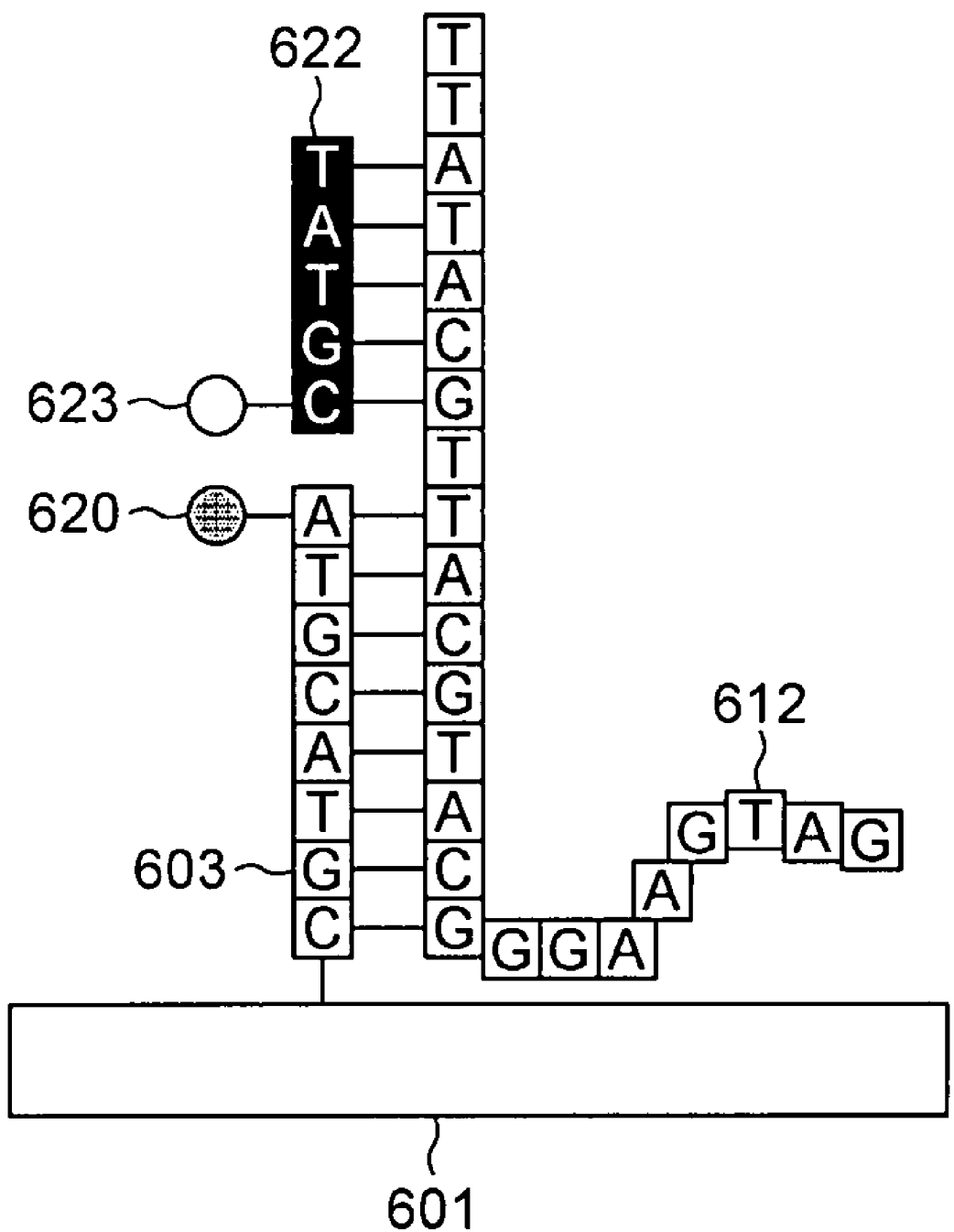
FIG. 6 is a schematic view showing the outline of a detection method of the present invention.

Furthermore, another method of detecting hybridization according to this embodiment will now be described with reference to FIG. 6. A probe nucleic acid 603 is immobilized on a substrate 601. The probe nucleic acid 603 has a nucleic acid sequence that specifically binds to a target nucleic acid 612. A labeled probe 622 has a structure that specifically binds to a site of the target nucleic acid 612, the site being adjacent to a site binding to the probe nucleic acid 603. A feature of this embodiment lies in a first dye 620 labeled on the probe nucleic acid 603 and a third dye 623 labeled on the labeled probe 622. The first dye 620 and the third dye 623 are a pair of fluorescent dyes that can cause a fluorescence resonance energy transfer (FRET). The first dye 620 and the third dye 623 may be bound to any position of the probe nucleic acid 603 or the labeled probe 622, but the first dye 620 and the third dye 623 must be disposed within a certain distance so that the dyes can induce the FRET phenomenon when being bound to each other. The FRET phenomenon occurs between the first dye 620 and the third dye 623 and fluorescence is emitted only when the probe nucleic acid 603 is bound to the target nucleic acid 612. When the target nucleic acid 612 is not bound to the probe nucleic acid 603, fluorescence is not emitted because the FRET phenomenon does not occur. Accordingly, the target nucleic acid need not be labeled, and the binding between the probe nucleic acid and the target nucleic acid can be accurately detected.

Third Embodiment

A hybridization system in which the part of the reaction chamber in the apparatuses of the above embodiments is included in a cartridge is provided in a third embodiment.

More specifically, a cartridge wherein a probe nucleic acid that can specifically bind to a target nucleic acid is immobilized includes a reaction chamber for accommodating the probe nucleic acid, a supply port for supplying the reaction chamber with a sample solution containing the target nucleic acid, and a recovery section for recovering the sample solution supplied to the reaction chamber.

Figure 8:
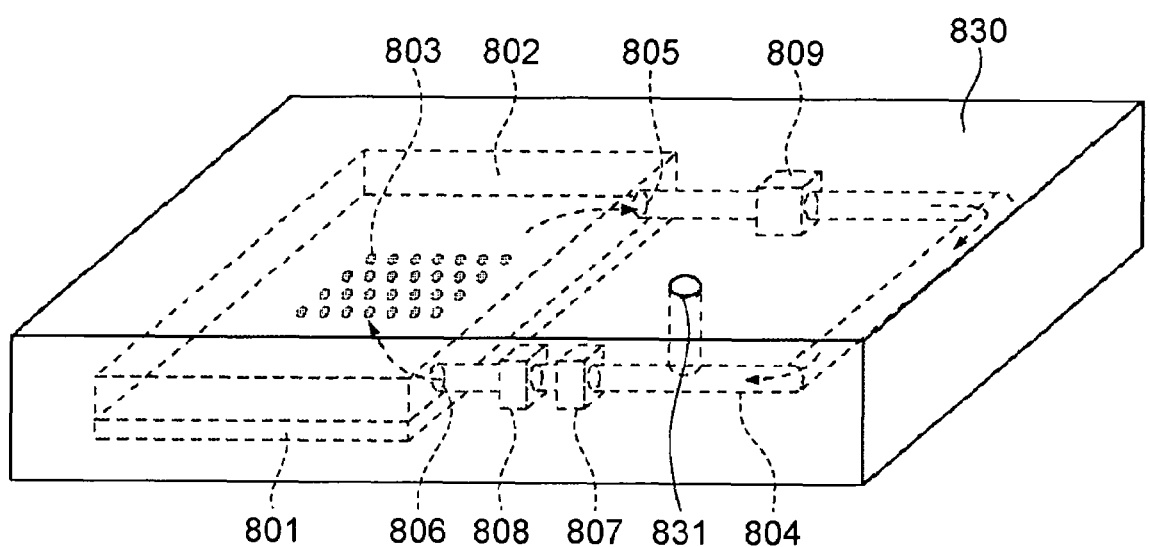
FIG. 8 is a schematic view showing a cartridge suitably used for performing a method of the present invention.

As shown in FIG. 8, the recovery section can form a circulation path that circulates the sample solution in the reaction chamber.

For example, as shown in FIG. 8, the present invention also provides a structure in which a part including a passage and a probe substrate is included in a cartridge and temperature control units and a supply unit constitute a separated apparatus. As shown in FIG. 8, a cartridge 830 includes a supply port 831, a substrate 801 having a probe nucleic acid 803 disposed thereon, a passage 804, and a reaction chamber 802 with an inlet 806 and an outlet 805.

A hybridization apparatus for hybridizing a target nucleic acid and a probe nucleic acid using the above cartridge includes a setting section for setting the cartridge, a supply mechanism for supplying the sample solution to the supply port of the cartridge, a recovery mechanism for recovering the sample solution supplied to the reaction chamber to the recovery section, and a heater for heating the recovered sample solution to the denaturation temperature or higher, wherein the recovery mechanism is configured so as to again supply the heated sample solution from the recovery section to the reaction chamber.

In FIG. 8, a first temperature-controlled section 807 and a second temperature-controlled section 808 are composed of members having high thermal conductivity and configured so that the temperature of the liquid in the passage can be controlled by corresponding temperature control units (not shown). A pump-unit connecting section 809 is configured so that an external pump unit can be connected thereto. More specifically, for example, the part of the passage is composed of an elastic member, and a unit for drawing the elastic member in one direction is used as the external pump unit. Accordingly, the liquid in the passage can be transferred by pumping action.

These cartridges can be produced by those skilled in the art using a resin molding technique or a micro total analysis system (μ-TAS) technique.

The present invention also provides a cartridge including a plurality of the above reaction systems for the purpose of batch processing of a plurality of samples and an apparatus that can hold a plurality of cartridges.

EXAMPLES

Examples of a method for hybridizing nucleic acids and a hybridization apparatus according to the present invention will now be described, but the content of the present invention is not limited to the following examples.

Example 1

First, 200 types of single-stranded DNA with a base length of 20 mer that specifically bind to corresponding 200 types of target sequences were synthesized as a probe nucleic acid. These 200 types of probe nucleic acid were immobilized on a quartz substrate by the method disclosed in Japanese Patent Laid-Open No. 11-187900.

Next, the substrate was set in the apparatus shown in FIG. 1. The first temperature control unit was set to 95° C. and the second temperature control unit was set to 50° C. Temperature control was performed in the chamber so that the temperature of the substrate was maintained at 50° C.

The total amount of liquid was 1 mL, and the passage and the pump were set so that the temperature of a reaction solution was controlled at 95° C. in the first temperature control unit for 30 seconds and the time required for the reaction solution, whose temperature was decreased to 50° C. by passing through the second temperature control unit, to reach the chamber was 3 seconds.

The sample containing the above 200 types of target nucleic acid was labeled with a Cy3 dye (manufactured by Amersham Pharmacia Biosciences) to prepare 1 mL of hybridization solution. The following composition, which is generally used, was used as the composition of the hybridization solution.
6×SSPE/10% formamide/0.05% SDS/labeled target substance (6×SSPE: NaCl 900 mM, NaH$_2$PO$_4$.H$_2$O 60 mM, EDTA 6 mM, pH 7.4)

The prepared hybridization solution was introduced into the apparatus, and the operation of the pump was started. Two hours later, the pump was stopped and the substrate was removed.

The substrate was washed with an appropriate buffer solution containing a surfactant. Fluorometry was performed with a fluorescence detection unit for a DNA microarray (GenePix 4000B, manufactured by Axon Instruments). A substrate was prepared as in the above substrate except that the reaction time was four hours, and the same measurement was performed. Furthermore, the same procedure was performed using a sample that did not contain the target nucleic acid.

The average luminance in the measured 200 types of probe nucleic acid was as follows. When no target nucleic acid was contained, the luminance was not detected. This result showed that error detection was not performed. The luminance measured after two hours was significantly larger than half the luminance measured after four hours. This result showed that the luminance reached a sufficiently detectable level after two hours.

TABLE 1

|  | Without target | 2 hours later | 4 hours later |
|---|---|---|---|
| Average luminance | 0 | 4,000 | 5,000 |

Comparative Example 1

A hybridization reaction was conducted with a HybArray 2 manufactured by PerkinElmer, Inc., which is a commercially available hybridization apparatus. The probe nucleic acid, the substrate, the target nucleic acid, and the composition of hybridization solution were the same as those in Example 1.

The fluorescent luminance was measured two hours later and four hours later, and the measurement was performed using a sample that did not contain the target nucleic acid, as in Example 1. The average luminance in the measured 200 types of probe nucleic acid was as follows.

TABLE 2

|  | Without target | 2 hours later | 4 hours later |
|---|---|---|---|
| Average luminance | 0 | 200 | 500 |

The luminance measured after two hours and four hours was significantly lower than that in Example 1. When the result after two hours was compared with the result after four hours, the luminance was substantially proportional to the time. Accordingly, it is believed that the reaction still proceeded after four hours.

As described above, according to the apparatus of the present invention, the time required for the hybridization reaction can be significantly reduced, and the luminance can be markedly increased to markedly improve the detection sensitivity.

Example 2

Another example of the present invention will now be described. This example shows a method of performing hybridization while a target nucleic acid is amplified with the apparatus shown in FIG. 4.

First, a substrate on which a probe nucleic acid was immobilized was prepared as in Example 1 and was set in the apparatus shown in FIG. 4. The same target nucleic acid as that of Example 1 was used, but the concentration thereof was decreased to ¹⁄₁,₀₀₀. A feature of the composition of a hybridization solution was that the hybridization solution contained a reagent for PCR. A buffer solution containing ExTaq enzyme (manufactured by Takara Shuzo Co. Ltd.,) and MgCl$_2$ was used as the PCR reagent, and the hybridization solution contained no organic solvent. A nucleotide that was one component of the PCR reagent contained Cy3-dUTP (manufactured by Amersham Pharmacia Biosciences), and the amplified product was labeled with Cy3.

The first temperature control unit was set to 95° C. and the second temperature control unit was set to 50° C. Temperature control was performed in the chamber so that the temperature of the substrate was maintained at 50° C. The third temperature control unit was set to 92° C., the fourth temperature control unit was set to 65° C., and the fifth temperature control unit was set to 72° C. The total amount of liquid was 1 mL, and the passage and the pump (the feed rate of the reagent flowing in the passage) were set so that the times required for controlling the temperature of the reaction solution in each control unit were as follows. The temperature of the reaction solution was controlled at 92° C. in the third temperature control unit for 45 seconds, the temperature of the reaction solution was controlled at 65° C. in the fourth temperature control unit for 45 seconds, and the temperature of the reaction solution was controlled at 72° C. in the fifth temperature control unit for 45 seconds. Furthermore, the passage and the pump were set so that the temperature of the reaction solution was controlled at 95° C. in the first temperature control unit for 30 seconds and the time required for the reaction solution, whose temperature was decreased to 50° C. by passing through the second temperature control unit, to reach the chamber was 3 seconds.

The prepared hybridization solution was introduced into the apparatus, and the operation of the pump was started. Two hours later, the pump was stopped and the substrate was removed.

The substrate was washed with an appropriate buffer solution containing a surfactant. Fluorometry was performed with a fluorescence detection unit for a DNA microarray (GenePix 4000B, manufactured by Axon Instruments). The same procedure was performed using a sample that did not contain the target nucleic acid. Furthermore, in order to confirm the effect of amplification, the same experiment was performed with a hybridization solution that did not contain the PCR reagent.

The average luminance in the measured 200 types of probe nucleic acid was as follows. When no target nucleic acid was contained, the luminance was not detected. This result showed that error detection was not performed. In the case where the hybridization solution did not contain the PCR reagent, the luminance was significantly low. This result showed that the target nucleic acid detected in this example was a nucleic acid that was amplified in this apparatus.

TABLE 3

|  | Without target | Without PCR reagent | Example |
| --- | --- | --- | --- |
| Average luminance | 0 | 50 | 4,000 |

Comparative Example 2

The same target nucleic acid as that in Example 2 was amplified by a PCR method. A commercially available PCR reagent and a commercially available PCR apparatus were used. The temperature cycle was 92° C., 65° C., and 72° C. in that order as in Example 2. This cycle was repeated 40 times, and it took 2 hours and 30 minutes.

The hybridization of the target nucleic acid amplified by the above procedure was performed with a commercially available hybridization apparatus. The probe nucleic acid, the substrate, the target nucleic acid, and the composition of hybridization solution were the same as those in Example 1.

Two hours later, the fluorescent luminance was measured as in Example 2. The same procedure was performed using a sample that did not contain the target nucleic acid, and fluorometry was then performed. The average luminance in the measured 200 types of probe nucleic acid was as follows.

TABLE 4

|  | Without target | 2 hours later |
| --- | --- | --- |
| Average luminance | 50 | 200 |

The luminance was significantly lower than that in Example 2. In addition, the operation time including the amplification step was 4 hours and 30 minutes, which was more than two times that in Example 2. Furthermore, the luminance was detected even in the sample that did not contain the target nucleic acid. This result showed that foreign substances were mixed during the operation.

As described above, the use of the apparatus of the present invention can conduct a hybridization reaction with high sensitivity even in a very small amount of target nucleic acid and can reduce the operation time. Furthermore, since the operation procedure is simplified, a reaction that is not affected by mixing of foreign substances and that has high reliability can be performed.

According to the results of these examples, when the method and the apparatus of the present invention are used, highly sensitive hybridization can be performed with high efficiency.

The present invention is not limited to the above embodiments and various changes and modifications can be made within the spirit and scope of the present invention. Therefore, to apprise the public of the scope of the present invention, the following claims are made.

This application claims the benefit of Japanese Application No. 2006-031046 filed Feb. 8, 2006, which is hereby incorporated by reference herein in its entirety.

What is claimed is:

1. A method for hybridizing a target nucleic acid and a probe nucleic acid that can specifically bind to the target nucleic acid and that is immobilized on a substrate by circulating a sample solution containing the target nucleic acid, comprising:
   a reaction step of allowing the target nucleic acid contained in the sample solution to react with the probe nucleic acid, wherein the reaction step is performed in a first region;
   a recovery step of recovering the sample solution after the reaction step;
   a heating step of heating the recovered sample solution to the denaturation temperature of the target nucleic acid or a higher temperature;
   an adjustment step of adjusting a temperature of the heated sample solution to an optimum temperature for hybridization, wherein the adjustment step is performed in a second region different from the first region, and the temperature of the heated sample solution is adjusted directly from the temperature obtained in the heating step; and a supplying step of supplying the sample solution containing the target nucleic acid in a denatured state resulting from the adjustment step to the first region to react with the probe nucleic acid, wherein the sample solution comprises a single-stranded nucleic acid complementary to the target nucleic acid, and wherein the flow rate for supplying the probe nucleic acid with the sample solution is set so as to satisfy the following relationship: the time required for the sample solution whose temperature is controlled to the hybridization temperature to reach the probe nucleic acid < the time required for the number of single-stranded target nucleic acid molecules in the sample solution to decrease by half.

2. The method according to claim 1, further comprising:
a step of amplifying the target nucleic acid performed between the recovery step and the adjustment step, wherein the sample solution contains an amplification reagent.

3. The method according to claim 1, wherein the substrate is a glass plate.

4. A method for hybridizing a target nucleic acid and a probe nucleic acid that can specifically bind to the target nucleic acid and that is immobilized on a substrate, comprising:

a first reaction step of allowing the target nucleic acid contained in a sample solution to react with the probe nucleic acid;

a recovery step of recovering the sample solution after the first reaction step;

a heating step of heating the recovered sample solution to the denaturation temperature of the target nucleic acid or a higher temperature; and a second reaction step of allowing the target nucleic acid contained in the sample solution after the heating step to react with the probe nucleic acid, wherein the sample solution comprises a single-stranded nucleic acid complementary to the target nucleic acid, and wherein the flow rate for supplying the probe nucleic acid with the sample solution is set so as to satisfy the following relationship: the time required for the sample solution whose temperature is controlled to the hybridization temperature to reach the probe nucleic acid < the time required for the number of single-stranded target nucleic acid molecules in the sample solution to decrease by half.

5. The method according to claim 1, wherein all of the respective steps are performed by circulating the sample solution in a circulation path formed on a substrate.

* * * * *